United States Patent
Medelius

(10) Patent No.: US 10,146,196 B2
(45) Date of Patent: Dec. 4, 2018

(54) WEARABLE ENVIRONMENTAL INTERACTION UNIT

(71) Applicant: HEARTMILES, LLC, Aliso Viejo, CA (US)

(72) Inventor: Pedro J. Medelius, Merritt Island, FL (US)

(73) Assignee: HeartMiles, LLC, Aliso Viejo, CA (US)

( * ) Notice: Subject to any disclaimer, the term of this patent is extended or adjusted under 35 U.S.C. 154(b) by 0 days.

(21) Appl. No.: 15/302,716

(22) PCT Filed: Apr. 10, 2015

(86) PCT No.: PCT/US2015/025368
§ 371 (c)(1),
(2) Date: Oct. 7, 2016

(87) PCT Pub. No.: WO2015/157670
PCT Pub. Date: Oct. 15, 2015

(65) Prior Publication Data
US 2017/0031334 A1    Feb. 2, 2017

Related U.S. Application Data

(60) Provisional application No. 61/977,937, filed on Apr. 10, 2014.

(51) Int. Cl.
*G05B 15/02* (2006.01)
*A61B 5/0476* (2006.01)
(Continued)

(52) U.S. Cl.
CPC ............... *G05B 15/02* (2013.01); *A61B 5/01* (2013.01); *A61B 5/021* (2013.01); *A61B 5/024* (2013.01);
(Continued)

(58) Field of Classification Search
CPC ... G05B 15/02; A61B 5/0476; A61B 5/14542; A61B 5/0402; A61B 5/01; A61B 5/165;
(Continued)

(56) References Cited

U.S. PATENT DOCUMENTS 7,558,622 B2 * 7/2009 Tran ................... A61B 5/0022
                                                          600/509
8,583,263 B2 * 11/2013 Hoffberg ............... G05B 15/02
                                                           340/3.71
(Continued)

FOREIGN PATENT DOCUMENTS

WO    WO 2016119961 A1 *  8/2016  ......... G07C 9/00007

OTHER PUBLICATIONS

International Search Report from the U.S. Patent Office for International Application No. PCT/US2015/025368, dated Jul. 20, 2015.
(Continued)

*Primary Examiner* — Ronald D Hartman, Jr.
(74) *Attorney, Agent, or Firm* — Finnegan, Henderson, Farabow, Garrett & Dunner, LLP

(57) ABSTRACT

A wearable environmental interaction unit may include a plurality of sensors each being configured to provide an output indicative of at least one physiological aspect of an individual; a transmitter to establish a wireless communication path between the wearable environmental interaction unit and at least one environmental response unit located remotely with respect to the wearable environmental interaction unit; and a microcontroller. The microcontroller may be programmed to: analyze the outputs provided by the plurality of sensors; determine a state of being for the individual based on the outputs of the plurality of sensors; generate an environmental interaction control signal based on the determined state of being for the individual; and cause the transmitter to transmit the environmental interaction
(Continued)

control signal to the at least one environmental response unit via the wireless communication path, the environmental interaction control signal being configured to cause a response by the environmental response unit including at least one change in an environmental condition.

15 Claims, 5 Drawing Sheets

(51) Int. Cl.
| | |
|---|---|
| *G05D 23/19* | (2006.01) |
| *H04L 12/28* | (2006.01) |
| *A61B 5/021* | (2006.01) |
| *A61B 5/024* | (2006.01) |
| *A61B 5/11* | (2006.01) |
| *A61B 5/16* | (2006.01) |
| *A61B 5/00* | (2006.01) |
| *A61B 5/01* | (2006.01) |
| *A61B 5/0402* | (2006.01) |
| *A61B 5/08* | (2006.01) |
| *A61B 5/145* | (2006.01) |

(52) U.S. Cl.
CPC .......... *A61B 5/0402* (2013.01); *A61B 5/0476* (2013.01); *A61B 5/0816* (2013.01); *A61B 5/1118* (2013.01); *A61B 5/14542* (2013.01); *A61B 5/165* (2013.01); *A61B 5/681* (2013.01); *G05D 23/1905* (2013.01); *H04L 12/2829* (2013.01); *A61B 2562/0219* (2013.01); *H04L 2012/2841* (2013.01)

(58) Field of Classification Search
CPC ....... A61B 5/1118; A61B 5/024; A61B 5/021; A61B 5/681; A61B 2562/0219; A61B 5/0816; H04L 12/2829; G05D 23/1905
See application file for complete search history.

(56) References Cited

U.S. PATENT DOCUMENTS

| | | | |
|---|---|---|---|
| 8,647,268 B2 * | 2/2014 | Tran | A61B 5/103 600/301 |
| 8,795,168 B2 * | 8/2014 | Goh | A61B 5/0002 128/903 |
| 9,207,659 B1 * | 12/2015 | Sami | G05B 15/02 |
| 9,473,321 B1 * | 10/2016 | Bazar | H04L 12/2829 |
| 9,582,034 B2 * | 2/2017 | von Badinski | G01P 15/00 |
| 9,599,632 B2 * | 3/2017 | Yuen | G01B 21/16 |
| 9,797,785 B2 * | 10/2017 | Giorgi | G01K 13/00 |
| 9,800,429 B2 * | 10/2017 | Crayford | H04L 12/2803 |
| 9,839,101 B2 * | 12/2017 | Clymer | H05B 37/0272 |
| 2008/0167535 A1 * | 7/2008 | Stivoric | A61B 5/0008 600/301 |
| 2008/0221401 A1 | 9/2008 | Derchak et al. | |
| 2011/0137141 A1 | 6/2011 | Razoumov et al. | |
| 2012/0031984 A1 * | 2/2012 | Feldmeier | F24F 11/001 236/49.3 |
| 2012/0203081 A1 | 8/2012 | Leboeuf et al. | |
| 2012/0313746 A1 * | 12/2012 | Rahman | A61B 5/0024 340/5.1 |
| 2013/0072765 A1 * | 3/2013 | Kahn | A61B 5/01 600/301 |

OTHER PUBLICATIONS

Written Opinion of the International Searching Authority from the U.S. Patent Office for International Application No. PCT/US2015/025368, dated Jul. 20, 2015.

* cited by examiner ized in various colors and patterns. The band may be adjustable,
WEARABLE ENVIRONMENTAL INTERACTION UNIT This application claims priority to U.S. Provisional Application No. 61/977,937, filed on Apr. 10, 2014, which is hereby incorporated by reference in its entirety.

TECHNICAL FIELD

This present application relates to a sensor-based device to monitor physiological aspects of an individual and to interact with one or more systems or devices present in an environment of the individual based on the monitored physiological aspects of the individual.

BACKGROUND

This application describes a system and devices (e.g., wearable devices) that can be used to provide an interface between one or more individuals and devices or systems in the surrounding environment. Traditionally, portable heart rate or activity monitoring devices have been used primarily to assess physical fitness and to determine levels of exertion or activity. With the incorporation of additional sensors and/or the use of digital signal processing techniques in one or more programmed controller devices, physical information obtained from an individual (e.g., heart rate, movement, rate of change of movement, body temperature, skin humidity, respiration rate, blood pressure, blood sugar ECG, EEG, etc.) can be used to determine, among other things, a state of mind or state of being associated with the individual being monitored. Such as state of mind or state of being may include, for example, a state of anxiety, stress, pressure, excitement, sadness, depression, relaxation, calmness, madness, upset, anger, hunger, thirst, exhaustion, sleepiness, alertness, among other feelings and physical states.

Being able to determine the state of mind or being of an individual or group may provide an opportunity to modify, or control one or more aspects of devices or systems in a surrounding environment in order to influence, respond to, and/or communicate with the monitored individual or group based on the sensed state of being. In some situations, specific messages, advertising, suggestions, or content may be provided to the individual to match a determined cumin state of mind or being. Such interaction with the monitored individual or group may be used to assist the individual or group in achieving an alternate, more desirable state, or in continuing and accentuating a present state.

SUMMARY OF THE INVENTION

One aspect of the disclosure may include a wearable environmental interaction unit. The wearable environmental interaction unit may include a plurality of sensors each being configured to provide an output indicative of at least one physiological aspect of an individual; a transmitter to establish a wireless communication path between the wearable environmental interaction unit and at least one environmental response unit located remotely with respect to the wearable environmental interaction unit; and a microcontroller. The microcontroller may be programmed to: analyze the outputs provided by the plurality of sensors; determine a state of being for the individual based on the outputs of the plurality of sensors; generate an environmental interaction control signal based on the determined state of being for the individual; and cause the transmitter to transmit the environmental interaction control signal to the at least one environmental response unit via the wireless communication path, the environmental interaction control signal being configured to cause a response by the environmental response unit including at least one change in an environmental condition.

Another aspect of the present disclosure may include an environmental response system comprising. The environmental response system may include one or more environmental control devices configured to change at least one aspect of an environment; a transceiver to receive an environmental control signal from one or more environmental interaction units each associated with an individual; and a processing device. The processing device may be programmed to: receive and process the environmental control signal from the one or more environmental interaction units; determine an environmental change to make based on the environmental control signal; and cause the environmental change through control of the one or more environmental control devices.

DETAILED DESCRIPTION

Figure 1:
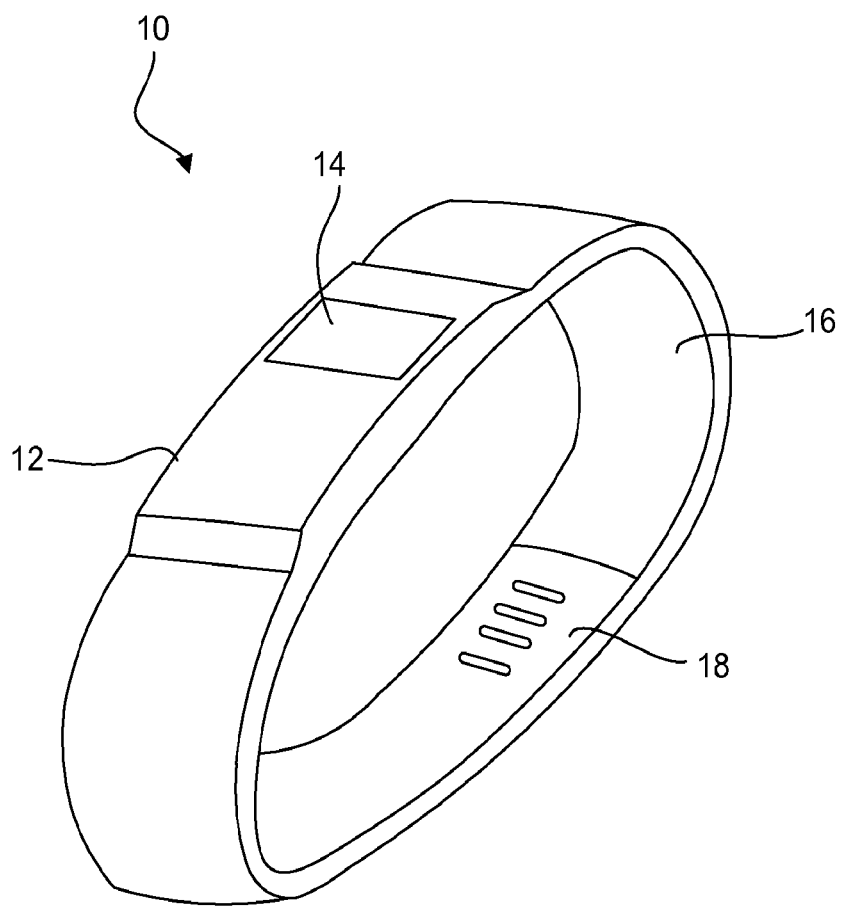
FIG. 1 is a diagrammatic representation of an environmental interaction unit according to an exemplary disclosed embodiment.

FIG. 1 provides diagrammatic representation of an environmental interaction unit 10 according to an exemplary disclosed embodiment. Environmental interaction unit 10 may include an electronics housing 12, an optional display 14, a body retention element 16, and a closure mechanism 18. Electronics housing 12 may include, among other elements, an array of physiological sensors and at least one microcontroller (described in detail below). Body retention element 16 may be configured to retain interaction unit 10 in contact with a body of an individual. In some embodiments, for example where interaction unit 10 is to be positioned on the wrist of the individual, retention element may include a wrist strap or band. Display 14 may include an LCD display or any other suitable display device for communicating visual information to the individual.

As illustrated in FIG. 1, the disclosed environmental interaction unit 10 may be configured as a wearable article. In certain embodiments, for example, the environmental interaction unit may be incorporated into an article wearable on an individual's wrist. Such an article would offer the advantage of being minimally intrusive, as most people are accustomed to wearing articles fastened to the wrist. The wrist unit could be fashioned as a simple wrist band stylized in various colors and patterns. The band may be adjustable, shockproof, and secured to the wrist using closure mechanism 18, which may include a hook and loop closure, a buckle closure, an elastic material requiring no separate closure device, a magnet, or any other suitable fastening configuration. The band can be made from various materials including, for example, a waterproof material, neoprene, polymer, nylon, leather, metal, or any other wearable material.

In one embodiment, environmental interaction unit 10 may include a small, self-contained unit. In such a configuration, there may be little or no external indication of the presence of the hardware components of the environmental interaction unit. In other embodiments, the environmental interaction unit may be incorporated into a watch, bracelet, heart rate monitor or other wearable article to provide added functionality to those devices. In addition to the wrist, the disclosed environmental interaction unit may be positioned over any portion of a user's body (e.g., the neck, chest, ankle, head, ear, nose, or thigh) that can provide suitable access to the biological markers needed for monitoring physiological information associated with the user. For example, the environmental interaction unit may be configured as or incorporated into shoe soles, ear clips, a necklace, ankle band, socks, a belt, glove, ring, sunglasses, hat, helmet, cap, and/or a headband.

In certain embodiments, sensors placed in proximity to a user's wrist may be used for monitoring heart rate, activity level, skin humidity, blood oxygenation. Sensors placed in the chest region may be used, for example, for monitoring heart rate, breathing rate, body temperature, EKG, EEG. Sensors on the legs, arms, or ankles may monitor striding, movement, activity level. Sensors located at the head of the user can monitor heart rate and temperature. Of course the sensor locations described are exemplary only. In many cases, other parameter values or types may also be sensed from the identified locations.

Figure 2:
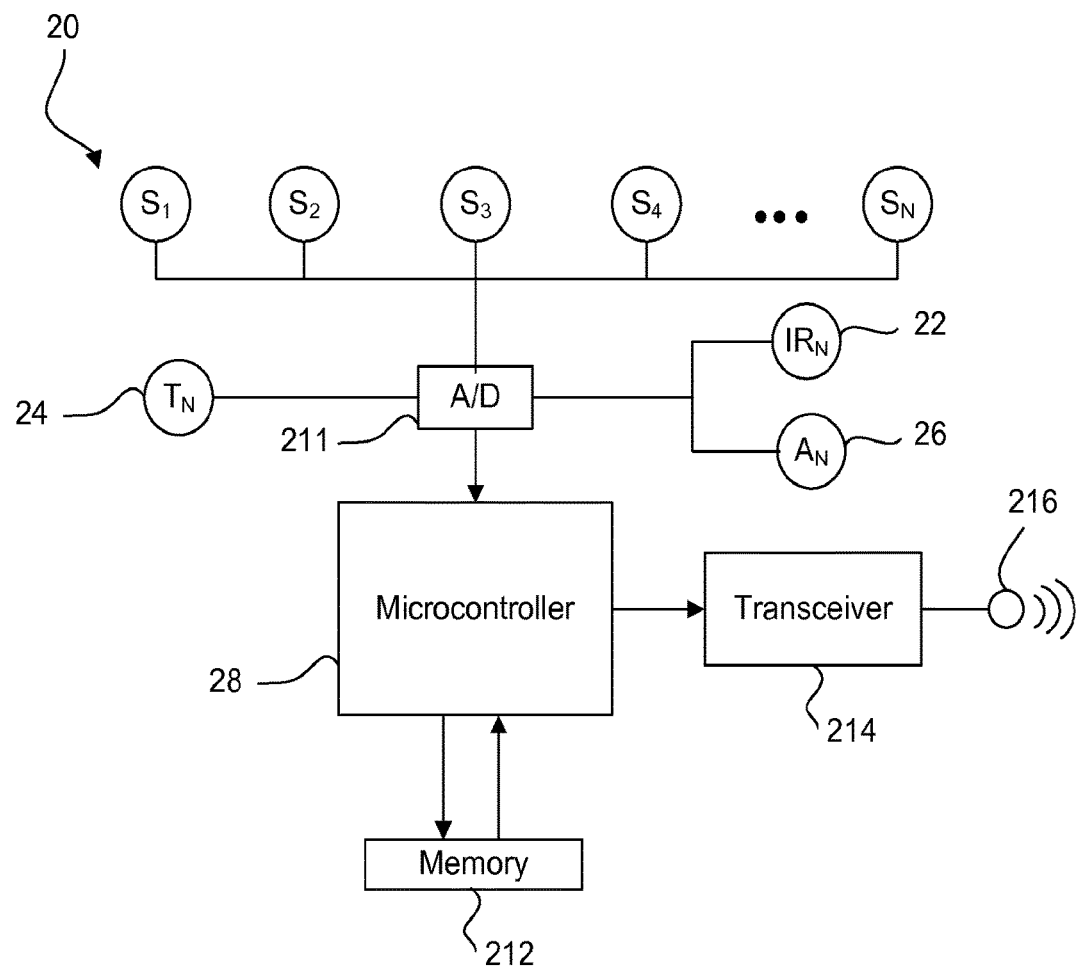
FIG. 2 is a block diagram representation of an exemplary environmental interaction unit according to an exemplary disclosed embodiment.

As shown in FIG. 2, environmental interaction unit 10 may include a plurality of sensors 20. In some embodiments, sensors 20 may be included in housing 12. In other embodiments, however, one or more of the plurality of sensors 20 may be distributed at various locations of environmental interaction unit 10. Among the plurality of sensors, each sensor may be configured to monitor only a single parameter value. Alternatively, an individual sensor in the plurality of sensors may be configured to monitor multiple parameter values.

The plurality of sensors 20 may include any suitable sensor units for monitoring one or more physiological aspects associated with the individual. In some embodiments, the plurality of sensors 20 may include sensor units for monitoring heart rate, body temperature, velocity, acceleration, blood oxygenation, skin conductivity, skin moisture level, $CO_2$ levels, blood pressure, eye movement (e.g., blinking rate, presence of tears, open or closed eyes), sound, breathing rate (e.g., by monitoring blood oxygenation levels), chemical presence (oxidizers, alcohols, acids), electric fields, light (color, intensity, wavelength (UV or IR), movement direction, movement patterns, blood sugar level, snoring, voice attributes, ECG, and/or EEG.

Such sensors may include, for example, one or more infrared sensors/transceiver units 22. Suppliers of appropriate infrared transmitter/receivers include Vishay Semiconductors, among others. Each infrared sensor may be configured as a transmitter/receiver capable of monitoring the oxygen content of blood passing through nearby blood vessels. Specifically, each infrared sensor can be configured to both emit infrared radiation into the body of the wearer of environmental interaction unit 10 and detect the level of infrared radiation received at the sensor. The wavelength of the emitted radiation can be selected according to the requirements of a particular application. In one embodiment, the infrared sensors can be configured to emit infrared radiation in a wavelength range of about 650 nm to about 950 nm.

The difference between the emitted radiation level and the detected radiation level is characteristic, of the amount of infrared radiation absorbed by the body and, especially, by oxygen-carrying blood. This sensed absorption level can be used to determine the pulse rate of the user of environmental interaction unit 10, the breathing rate of the user, or other parameter values related to blood oxygenation. In some situations, the infrared absorption level may be affected by the expansion and contraction of nearby blood vessels and the oxygen content of blood passing through nearby vessels, which are both physical characteristics that vary together with heart rate. Thus, the rate of observed changes in infrared absorption characteristics of the body can enable a calculation of the user's heart rate.

While only one infrared sensor may be needed depending on the functional requirements of a particular embodiment, including two or more infrared sensors, or even three or more infrared sensors, can serve to increase the reliability of the data collected from these sensors. Such infrared sensors may be spaced apart from one another. In certain embodiments, these sensors may be located along a perimeter of housing 12 of environmental interaction unit 10. Spacing the infrared sensors apart from one another can maximize the possibility that at least one sensor contacts the user's skin at all times, even during the movements associated with physical activities.

The plurality of sensors 20 may also include one or more accelerometers, temperature sensors (body or ambient), UV or IR photodetectors, microphones, EKG sensors, EEG sensors, $CO_2$ sensors, GPS sensors, microphones, and chemical sensors, among others.

The sensors included in environmental interaction unit 10 may be located together in a single housing 12. In one embodiment, the plurality of sensors 20 may be integrated together to form a sensor array, for example, on a common printed circuit board. While this sensor array could be located at any position along body retention element 16, in one embodiment, the sensor array may be located at a point along body retention element 16 that is adjacent to the underside of the wrist of a user. In this configuration, the sensor array, or portions thereof, could be made to contact the underside of the user's wrist when environmental interaction unit 10 is worn.

Housing 12 may include a window (not shown) fabricated from an infrared transmissive or transparent material, for example, to allow radiation emitted from infrared sensors 22, for example, to pass out of housing 12 and impinge upon a portion of the user's wrist (e.g., the underside of the user's wrist). In turn, such a window may allow infrared radiation reflected or emitted from the user's skin to pass into housing 12 via the window. Such infrared transmissive or transparent materials for the window may include, e.g., germanium, zinc selenide, sapphire, IR glass, IR polymer, barium fluoride, calcium fluoride, and combinations thereof. In certain embodiments, one or more of infrared sensors 22 may be embedded directly into the material of the window. Such a configuration may offer enhanced sensitivity by placing the infrared sensors 22 close Co the user's skin, among other potential benefits.

Housing 12 can be constructed of a material different from body retention element 16. For example, housing 12 may be fabricated from a polymer, metal, rubber, cloth, leather, or any other material suitable for a desired application. In certain embodiments, housing 12 can be constructed from a conducting material to establish an electrical or thermal conduction path, if desired, between any of the sensors of environmental interaction unit 10 and the skin of the user.

Housing 12 can also be formed integrally with body retention element 16. In such an embodiment, housing 12 may be formed of the same material as body retention element 16 and may have the same thickness, or a slightly thicker profile, as compared to body retention element 16.

To provide power for environmental interaction unit 10, a battery may be provided. The battery may include a single battery. Alternatively, the battery may include multiple individual batteries connected in series, in parallel, or, alternatively, configured to separately and independently provide power to various electrical components of environmental interaction unit 10. The battery may be mounted within or outside of housing 12. Environmental interaction unit 10 may include a replaceable or rechargeable battery. In certain embodiments, three-volt lithium batteries contained within a 1.2 cm package may be included in environmental interaction unit 10. Additionally, or alternatively, a solar cell may be included either alone or in combination with one or more batteries. In addition to serving as a stand-alone power source, the solar cell may also function to recharge the batteries. In another embodiment, a motion activated regeneration device may be included for purposes of powering the environmental interaction unit and/or recharging batteries.

A power management scheme may be employed to lower the power requirements of infrared sensors 22. For example, the transmitter portion of each sensor may be pulsed at a predetermined duty cycle to conform to the power specifications of a particular configuration. In one exemplary embodiment, the infrared transmitters of sensors 22 can be pulsed using a 1% duty cycle at a rate of about 8 pulses per second.

In configurations where environmental interaction unit 10 includes a temperature sensor 24, the temperature sensor may be configured to monitor the body temperature of the wearer of environmental interaction unit 10 by measuring the temperature outside of housing 12 and, for example, against the skin of the wearer. Additionally, the temperature sensor may be configured to measure the temperature inside housing 12. Using the difference between the temperature measurements from inside and outside of housing 12, for example, it can be determined whether an observed temperature change outside of the housing is likely attributable to atmospheric conditions or an actual change in body temperature of the wearer of environmental interaction unit 10. While certain embodiments may include only one temperature sensor 24, other embodiments may include multiple temperature sensors in order to meet a desired set of operational characteristics (e.g., monitoring body temperature from multiple locations on environmental interaction unit 10; separate temperature sensors to monitor the temperature inside and outside of housing 12; etc.).

Temperature sensor(s) 24 may include any suitable device for ascertaining the body temperature of an individual. For example, temperature sensor(s) 24 may include a digital or analog device and may include thermocouples, diodes, resistance temperature detectors (RTDs), or infrared detectors. Suitable temperature sensors may be obtained from various suppliers, including Analog Devices Inc., Omega, or Texas Instruments. For certain types of temperature sensors, contact with the individual's skin may aid in obtaining accurate body temperature measurements. On the other hand, in certain instances where, for example, infrared sensors provide the primary mode of measuring body temperature, mere proximity to the individual's skin may be sufficient to accurately determine body temperature of the user.

Additionally, environmental interaction unit 10 may include one or more accelerometers 26 to monitor motion of environmental interaction unit 10. In certain embodiments, accelerometer 26 includes only a single axis accelerometer configured to detect motion along one axis. Other embodiments, however, may include multiple accelerometers. In one exemplary embodiment, accelerometer 26 may include a three-axis accelerometer, which includes three accelerometers arranged orthogonally with respect to one another. With such an arrangement, accelerometer 26 may be able to detect or monitor movements along three separate axes.

A three-axis accelerometer may be especially useful for the detection of movements associated with exercise and certain types of physical activity. Generally, most sports or types of physical activity produce a signature pattern of movements that can be detected using an accelerometer. In this way, accelerometer 26 can help confirm whether the wearer of environmental interaction unit 10 is engaged in physical activity and, in certain cases, can help determine the type of sport or activity in which the wearer is engaged. Such sport or activity determination can be performed onboard environmental interaction unit 10 or, alternatively or additionally, may be performed in a server or other computing device located remotely from environmental interaction unit 10.

Environmental interaction unit 10 can include any of multiple different configurations. For example, the environmental interaction unit may be configured in any suitable configuration for collecting physiological data from a user's body. Environmental interaction unit 10 may include one unit, as shown in FIG. 1, or it may include multiple separate components configured to be worn in different parts of the individual's body. Further, environmental interaction unit 10 may be worn in any suitable location in which physiological information may be collected by the plurality of sensors 20. In some embodiments, environmental interaction unit 10 may include EKG and/or EEG pulse sensors located in a chest strap (not shown). In some cases, the environmental interaction unit may be configured to collect physiological data while in contact with any portion of the user's body or in other cases from a location spaced apart from the user's body. The environmental interaction unit may be configured to be placed in contact with a user's head, neck, ear, nose, chest, wrist, or any other location on the body from which physiological data may be obtained.

Environmental interaction unit 10 may also include at least one microcontroller 28. Such a microcontroller may collect and monitor output signals provided by the plurality of sensors 20. In some embodiments, the outputs of sensors 20 may be provided to the at least one microcontroller 28 via an A/D converter 211.

Any suitable microcontroller 28 may be included in environmental interaction unit 10. In one embodiment, microcontroller 28 includes a small microcontroller having dimensions of about 0.4 inches by 0.4 inches, or smaller. One suitable microcontroller includes the PIC18F series of microcontroller manufactured by Microchip Inc. Other suitable microcontrollers may include a DSP16 or DSP32 chip families from Microchip. Microcontroller 28 may also include any of the ATTINY family of controllers from ATMEL, the STMF030 family of controllers from STMicroelectronics; and the P89LPC family of controllers from NXP Semiconductor. Preferably, microcontroller 28 would exhibit low power characteristics and would require from about 10 microamps to gout 50 microamps during normal operation and between 5 milliamps to about 20 milliamps while transmitting data. Microcontroller 28 may include a 32-bit (or higher) digital signal processor.

Microcontroller 28 of environmental interaction unit 10 may have several responsibilities. Among these responsibilities, microcontroller 28 may periodically collect data from the available sensors 20 via analog-to-digital converter 211. The frequency of data collection can be selected to meet the requirements of a particular application. In one embodiment, microcontroller 28 may sample the data from the sensors at least once per second (e.g., once every 0.1, 0.25, 0.5, or 0.75 seconds). Higher or lower sampling frequencies, however, may also be possible.

Microcontroller 28 may be configured with the ability for selecting from among multiple data sampling frequencies depending on sensed conditions. For example, microcontroller 28 may be programmed to sample the sensor outputs slower than once per second (e.g., once per every 2, 5, or 10 seconds) when microcontroller 28 determines that the user of the device is at rest (e.g., sleeping). Similarly, microcontroller 28 may be configured to sample the sensor outputs more frequently when the user is determined to be awake and active.

When appropriate, microcontroller 28 may also enter a rest state to conserve power. For example, when infrared sensors 22 provide no pulse readings or accelerometer 26 registers no movements over a certain period of time, microcontroller 28 may determine that environmental interaction unit 10 is not being worn. Under such conditions, microcontroller 28 may slow the sensor sampling period to once every thirty seconds, once every minute, or to another suitable sampling frequency. Additionally, microcontroller 28 may be configured to sample only a portion of the available sensors during times of physical inactivity or when environmental interaction unit 10 is not being worn. In one embodiment, for example, once microcontroller 28 determines that the user is not wearing environmental interaction unit 10, microcontroller 28 may begin sampling the output of temperature sensor 24 alone. In such a configuration, a perceived rapid change in temperature may indicate that environmental interaction unit 10 is in use and may prompt the controller to "wake up" and restore full functioning data collection.

Microcontroller 28 may also be configured to sample data from only a portion of the available sensors during times of physical activity. For example, during certain activities or conditions, microcontroller 28 may recognize that one or more of the available sensors is providing data suitable for recognizing and/or characterizing physiological attributes of the user. For example, in certain situations, infrared sensors 22 may provide robust data from which accurate pulse readings may be determined while accelerometer 26 or temperature sensor 24 may provide less robust data (e.g., low signal level, lower than average signal-to-noise ratio, intermittent signal, etc.). In such situations, microcontroller 28 may determine a particular set of sensors to rely upon more heavily when choosing which sensors to sample and what sensor output to use (and how to use it) when analyzing data, capturing data, and/or transmitting data.

Microcontroller 28 can be configured to analyze the data collected from the sensors onboard environmental interaction unit 10. For example, data from infrared sensors 22 can be used to compare the transmitted infrared signal to the received infrared signal and calculate the blood oxygen saturation level via known algorithms. Microcontroller 28 may also be configured to calculate the pulse rate by monitoring the frequency of changes in the blood oxygen saturation level.

A memory 212 may also be included on environmental interaction unit 10. In some embodiments, memory 212 may include a 64 kB or larger non-volatile memory that stores an operating system and application specific algorithms. Memory 212 may also include a 4 kB or larger volatile memory used, for example, to cache data waiting to be processed.

Microcontroller 28 can be configured to store raw or processed data in memory 212 included in environmental interaction unit 10. Memory 212 may include any suitable storage unit including, for example, a solid state non-volatile serial or parallel access memory. In certain embodiments, the memory may include a storage capacity of at least 32 MB. Suitable memory units include RAM, NVRAM, and Flash memory. It is also possible to use an internal microcontroller memory to store data, especially if microcontrollers are developed that include internal memory sizes greater than the currently available 64 kB sizes.

In addition to storing data, memory 212 can store instructions for execution by microcontroller 28. Thus, in addition to microcontroller being able to execute instructions intrinsic to the microcontroller architecture (e.g., microcontroller instruction sets), the microcontroller may be configured as a specific machine by being provided with access to programming instructions stored in memory 212. Such instructions and their associated functionality are discussed in detail below.

In the case that microcontroller 28 is configured to store raw data, microcontroller 28 may sample the outputs of the sensors 20 and simply store those values in memory 212. Those stored values can then later be downloaded from environmental interaction unit 10 and processed using devices and/or systems external to environmental interaction unit 10.

While it is possible to store raw data collected from the sensor devices, microcontroller 28 may also be configured to process the data sampled from the sensors of environmental interaction unit 10 and store processed data in memory 212. For example, microcontroller 28 may be configured to calculate pulse rate, temperature, acceleration and average each calculated value over periods of up to thirty seconds, sixty seconds, or more to remove noise and enhance accuracy of the readings. Microcontroller 28 can be further configured to store these time averaged, filtered pulse rate/temperature/acceleration readings at preselected intervals (e.g., once or twice per minute). Such a scheme may conserve memory and/or power resources yet still provide useful information. These processed or conditioned data signals stored in memory, in certain cases, can even be more useful, as they may exhibit less noise and rapidly fluctuating values, which can detract from the reliability of the data.

Microcontroller 28 may be configured to condition the signals received from one or more of the sensors onboard environmental interaction unit 10. During movement associated with physical activity, a significant amount of noise may be imparted to the signals generated by the onboard sensors. Such noise is especially prevalent in the data provided by the infrared sensors, which can be used to determine heart rate. Digital signal processing techniques may be employed to eliminate at least some of the noise from these signals and increase the accuracy of the heart rate calculation.

Environmental interaction unit 10 may also include a transceiver 214 for establishing wireless communication with devices external to environmental interaction unit 10. Transceiver 214 may include an antenna 216 and may operate according to any suitable communication protocol. For example, in some embodiments, transceiver 214 may enable wireless communication using such protocols as Bluetooth, ZigBee, WiFi, and/or custom/proprietary protocols. In some embodiments, communication can also take place through optical means using infrared or visible light transceivers, for example.

In some embodiments, microcontroller 28 may be configured to collect output data from the plurality of sensors 20 associated with environmental interaction unit 10. Microcontroller 28 may process the data output from the sensors in order to determine at least one attribute associated with the user of the interaction unit. For example, microcontroller 28 may analyze the outputs of the plurality of sensors 20 and determine a state of being for the individual user based on the sensor outputs.

The determined state of being can include any state or condition identifiable based on one or more data values of the sensor outputs. For example, states of being may include predefined types associated with particular combinations of sensor output values or to combinations of particular ranges of sensor output values. In some cases, the state of being may include normal, stressed, calm, happy, angry, alert, sleepy, inattentive, or excited states. Other states of being may also be predefined and used by microcontroller 28 to assign a state of being to the individual based on a current set of sensor outputs. Others states of being may include: anxious, pressured, sad, depressed, relaxed, hungry, thirsty, pain, fatigue, etc.

Microcontroller 28 may use any suitable method for determining a state of being for an individual based on the available sensor outputs. For example, in some cases, baseline levels for one or more of the plurality of sensors may be determined, and these baseline measurements can be compared to corresponding real-time sensor output values. The differences between the real-time sensor outputs and the corresponding baseline values may be compared to relevant, predetermined thresholds or threshold ranges. Based on these comparisons, a state of being may be determined or assigned for the individual.

Baseline measurements may include average sensor output values obtained for the individual during a time of rest (e.g., while the user is sleeping or in a restful, sedentary state) or may correspond to averages of sensor output values over any selected period of time, including running averages taken over all operating times. The comparison between real-time sensor outputs and determined baseline output values may provide an indication a departure from normal, baseline conditions particular to the individual user. The departures from the norm may be important in assigning a state of being to the individual. Baseline determinations may also be based, at least partially, upon user input. For example, baseline sensor output values may be collected during a time period when a user indicates that he or she is feeling relaxed or normal.

Determination of baseline values for an individual may also include the use of neural networks, where microcontroller 28 learns the typical sensor outputs associated with a particular individual. The learned output values may be used as the baseline values in the state of being determination.

The state of being determination may be made based on any suitable use of the sensor output values. In some cases, the determination may be based directly on the raw sensor output values. In other cases, the determination may be based on observed departures from the baseline norms of sensor output values.

In some embodiments, one or more lookup tables may be used in the state of being determination. These lookup tables may be multivariable or even multidimensional lookup tables that associate various states of being with combinations of sensor output values. In some embodiments, equations or a set of relationships may factor into the state of being determination. For example, the state of being may be expressed as a function, S, that depends on heart rate, skin conductivity, movement, breathing rate (or any other combination of sensor outputs). Comparing the value of S (the predetermined state of being function for a particular set of sensor output values) to a predetermined set of thresholds or threshold ranges can also lead to assignment of a state of being for the individual. For example, a value of S less than a certain threshold #1 may indicate a calm or sleepy state. A value of S between threshold #1 and a higher threshold #2, however, may indicate a normal state of being. A value of S greater than threshold #2, but less than a threshold #3 may indicate a state of physical activity, especially when coupled with observations of motion sensors, such as accelerometer 26. Values of S higher than threshold #3 may indicate a stressed state of being.

In some embodiments, a deviation in heart rate of 20% or 30% or more over a baseline heart rate value along with an increase in activity/movement may indicate exercise by the user, whereas an increase of 30% or more over a baseline heart rate, an increase of more than 25% over baseline skin conductivity, an no significant increase in activity level may indicate a stressed state of being. Deviations of more than a 10% increase in breathing rate without an increase in physical activity may also indicate onset of stress. Such deviation ranges and their associated states of being may be determined experimentally.

The plurality of sensors 20 may include a microphone for sound analysis. For example, a detected voice may be analyzed using a voice analysis tool to determine the presence of state of being indicators in the voice (e.g., volume, syncopation, recognized words, etc.). Additionally, the microphone may also capture sounds that a sound analysis tool may recognize as snoring (e.g., rhythmic vibrational sounds in a certain frequency range that occur with a periodicity falling within an expected breathing rate range). Such information may aid in determining whether an individual is excited, stressed, relaxed, drunk, asleep, etc.

Determination of the state of being may depend not only on the observed deviations in sensor output values from baseline or normal levels, but the state of being determination may also depend on time. For example, time durations associated with deviations from the normal or baseline levels may be monitored, and a change in a designated state of being may be made only if a deviation over a particular baseline threshold (e.g., 10%, 20%, 30%, 50% or more) occurs over a period of time exceeding a predetermined time threshold (e.g., 1 min, 2 min, 5 mm, or more).

In general, certain states of being may be associated with particular ranges of sensor output values. A user in a relaxed state may have sensor readings that indicate a low breathing rate, low heart rate, little movement activity, normal blood pressure, and normal skin conductivity (normal, low, and high being determined relative to historical or baseline measurements for the particular user, for example). A stressed state may be accompanied by increased skin conductivity and increased heart rate without a corresponding increase in physical activity as measured by the accelerometer. A tired state may be accompanied by low movement and low heart rate. An eye sensor indicating a rapid blinking rate over the baseline, or partially closed eyes, may indicate a sleepy state. Closed eyes for several seconds or more may indicate a sleep state. A sound sensor picking up a repetitive pattern of snoring may likewise indicate a sleep state.

The thresholds may be determined as values applicable to the general population. In other cases, however, the thresholds may be determined for an individual based on the baseline values determined for the individual. For example, the various thresholds may be calculated for a particular individual based on predetermined relationships (e.g., equations, weight factors, etc.) applied to the baseline sensor output values for the individual.

In some cases, microcontroller may incorporate a determination of whether the individual is engaged in physical activity in determining the state of being for the individual. Such a determination can help differentiate between ordinary exercise, which may be associated with a rise in heart rate, body temperature, skin conductivity, skin moisture, blood pressure, breathing rate, etc., and an excited or stressed state, for example, which may also be accompanied by rises in one or more of heart rate, body temperature, skin conductivity, skin moisture, blood pressure, breathing rate. Analysis of the output of accelerometer 26, or any other sensor that may aid in recognizing that an individual is exercising, may be helpful in distinguishing ordinary exercise from a stressed or excited state. For example, an increase in heart rate, perspiration, blood pressure, or breathing rate (among other potential parameters) without an indication of physical activity (either simultaneously or within a few minutes of each other) may signal a stress condition.

While it is contemplated that microcontroller 28 may determine the state of being for an individual onboard environmental interaction unit 10, other techniques may also be employed. For example, in some embodiments, raw or semi-processed data based on or including the sensor output values and baseline sensor output values may be transmitted (e.g., using transceiver 216) to a remote location. At the remote location, one or more processors may be used to determine a state of being for the individual based on the received data.

Based on the determination of the state of being for an individual, microcontroller 28 may generate an environmental interaction control signal based on the determined state of being. The environmental interaction control signal may include a signal to be transmitted from environmental interaction unit 10 via transceiver 216 to one or more remotely located systems or devices. In some embodiments, the remotely located systems may respond to the received environmental interaction control signal by changing at least one aspect of the environment of the individual. Such changes may include for example, changes in lighting, sounds, smells, air temperature, humidity, speed, etc.

Figure 3:
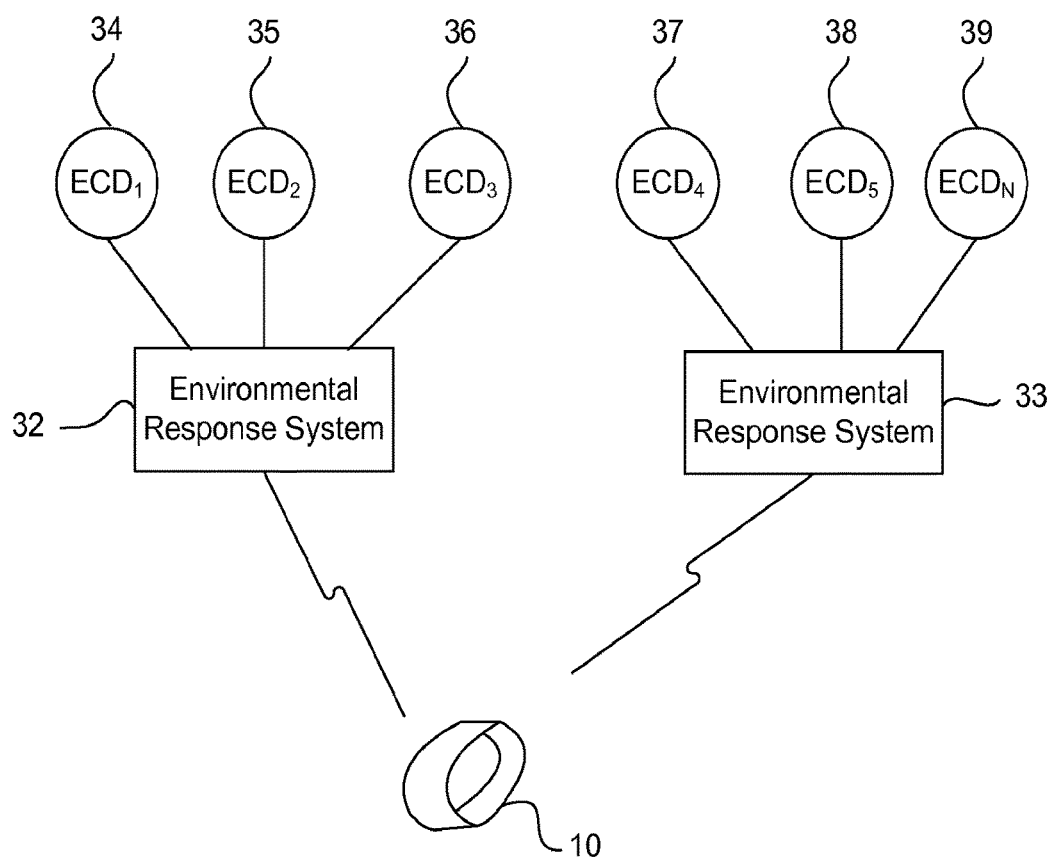
FIG. 3 is a representation of an environmental response architecture according to an exemplary disclosed embodiment.

FIG. 3 provides a diagrammatic representation of an environmental control system according to an exemplary disclosed embodiment. For example, this system may include one or more environmental response systems 32, 33, which can communicate wirelessly with environmental interaction unit 10. Such communication may be established between environmental response systems 32, 33 and environmental interaction unit 10 based on a range. For example, whenever an environmental interaction unit 10 moves within a communication range of an environmental response system 32, 33 data (e.g., the environmental interaction control signal) may be automatically uploaded to the environmental response system 32, 33. Such a data transfer may be initiated when environmental interaction unit 10 detects a nearby environmental response system 32, 33 or when an environmental interaction unit 10 detects a nearby environmental interaction unit 10.

Each environmental response system 32, 33 may include a transceiver for establishing wireless communication with one or more environmental interaction units 10 and may also include one or more processors for receiving and processing signals from the environmental interaction units 10. Based on the type of signal received (e.g., a particular state of being indicator or environmental control signal), the onboard processor may determine an appropriate response for any of ECDs 34-36 or ECDs 37-39.

Once a communication channel is established, data may be transmitted at any suitable rate. For example, updated state of being information, sensor output data, and/or environmental interaction control signals may be transmitted from environmental interaction unit 10 at a periodic rate (e.g., continuously, once per second, once per minute, or longer).

Based on the received, environmental interaction control signal, the environmental response system may cause one or changes in the environment of the individual by affecting one or more changes in at least one associated environmental control device 34-39 (e.g., $ECD_1$ to $ECD_N$) 33 shown in FIG. 3.

ECDs 34-39 can include any types of devices capable of impacting at least one aspect of a user's environment. In some embodiments, an ECD may include a light, an array of lights, light panels, colored lamps, lamps of different wavelengths of lights, smell or fragrance emitters, speakers, sound emitters, music players, TV, radio, heaters, air conditioners, humidifiers, video displays, windows, doors, fans, smart phones, tablets, vehicles, product displays, advertising/massage boards, etc.

The environmental interaction control signal may include one or more instructions for controlling a specific aspect of an environmental response system. Alternatively or additionally, the environmental interaction control signal may include a state of being for an individual, and the environmental response system receiving the data may determine an appropriate response based on the received state of being for the individual.

Communication between the environmental interaction unit 10 and one or more environmental response systems 32, 33 may be accomplished using any suitable communication technique. In some embodiments, such communication may be wireless and may be based on radio frequency, Bluetooth, Zigbee, cellular, Wi-Fi, optical, or infrared transmissions. The communication may depend on a handshaking process that may involve periodic checks of compatible devices within range (i.e., once a second, once every few seconds) and determination of the type of information required by the responsive system. Whether a communication channel may be established may also depend on a device authentication process to confirm that a particular environmental interaction unit 10 has permission to interact with a particular environmental response system, for example.

In certain embodiments, data transmission can extend beyond the limits of the onboard transceiver. For example, using a Bluetooth enabled environmental interaction unit coupled with an external device, such as a cell phone, PDA, personal computer, etc., data can be relayed from environmental interaction unit 10 through the external device and on to an environmental response system 32,33.

The environmental response system will acknowledge the presence of an environmental interaction unit, and may exchange information regarding the type of data it will require in order to take action (e.g., dimming of lights, changing light hue, changing lighting intensity, increasing/decreasing sound or music volume, adjusting vehicle speed or control (e.g., by adjusting a vehicle brakes or throttle, by engaging one or more driver assist controls, by activating air-bags or safety systems, by adjusting vehicle climate controls, etc., for example, if a driver is determined to be in a sleepy state), activation of product displays (via video screen or by highlighting a physical display of products using lights, for example), changing temperature in an environment (e.g., by automatically adjusting a thermostat), changing the humidity in an environment (e.g., by operating a humidifier or de-humidifier), securing doors (e.g., looking), securing windows, activating barriers, prompting advertisements, suggestions, audible or visual alerts, audible or visual warnings, or messages, etc.) After the handshaking process, the environmental interaction unit and the responsive system may agree on the rate of data transmission for updates. The environmental interaction unit may transmit data at the pre-established intervals. Both the environmental interaction unit and the responsive system may acknowledge the presence of each to verify that the information is still relevant, and that the use is still within range. Either the environmental interaction unit or the responsive system can periodically poll the environment to determine the presence (or not) of compatible devices. Data may be transferred between the environmental interaction unit and the environmental response systems using serial communication protocols. The data transmission can be fully encrypted to prevent eavesdropping.

Microcontroller 28 may be configured to control transmission of data to one or more environmental response systems 32, 33. In one embodiment, microcontroller 28 can activate transceiver 214, as illustrated in FIG. 2, with a low duty cycle of less than about 1% to detect the presence of suitable environmental response systems. An environmental response system can include any intended recipient of the data acquired by environmental interaction unit 10.

When environmental interaction unit 10 detects an environmental response system (or vice versa) (e.g., either through a wired or wireless data connection) and communication is established, download of data may commence, for example, after proper identification of the user/environmental interaction unit. This may prevent eavesdropping by unauthorized parties. Identification of the user may include transmission of a unique code assigned to each environmental interaction unit and/or user of the environmental interaction unit. A user-selectable password can be used to allow data to be uploaded to an environmental response system. In other embodiments, passive identification of a user may displace the need for password protected downloads. For example, the microcontroller may be configured to determine and store a biological signature of an authorized user of the environmental interaction unit. Such a signature may be determined using one or more of the plurality of sensors 20. Alternatively, one or more additional sensors (e.g., a skin pigment sensor, pH sensor, etc.) may be included to aid in user recognition.

One or more other devices, including, e.g., an RFID tag may be employed to facilitate the transmission of data or control signals to an environmental response system. For example, in response to a radio frequency interrogation signal, an REID tag located on environmental interaction unit 10 may power on using an onboard power source, such as a battery, or using energy provided by the interrogation signal. The RFID tag can respond to the interrogation signal by transmitting data to a location/receiver remotely located with respect to environmental interaction unit 10. The information transmitted may include information about environmental interaction unit 10. For example, the transmitted information may include a signature code associated with a particular environmental interaction unit 10. Additionally, the transmitted information may include any other data that may aid in recognition of the particular environmental interaction unit 10. Such an RFID tag may be attached or integrated with environmental interaction unit 10 at any suitable location. For example, an RFID tag may be included in housing 12 (FIG. 1) or at any other suitable location on environmental interaction unit 10.

Based on a determined being state for an individual, the environmental response systems can be used to modify or control the environment surrounding the individual based on the determined state of being for the individual. In some embodiments, such environmental modification may include presenting tailored messages, changes in lighting, sound or informational content to match the current state of mind or being of the individual. Such environmental modifications can also be used to assist the individual in achieving an alternate (perhaps more desirable) state of being or in continuing a present desired state of being.

There may be a multitude of ways for modifying aspects of an environment of an individual based on a determined state of being for the individual. For example, such environmental modifications may include changing light wavelengths in a room to a more soothing light color, selecting audio entertainment, news, talk shows, genres of music (or other content) to be played directly to user(s) or in the background via radio, TV, or Internet, adjusting room temperature, selecting visual entertainment, suggesting computer games, gameplay or activity, selecting and displaying specific advertising and products/services, releasing different types of smell and fragrance, suggesting recipes, selecting/dispensing foods or beverages, opening and locking means of ingress and egress, modifying vehicular speed, etc. Environmental control or modification can be applied in a variety of contexts, including stationary contexts, such as physical structures and open spaces or mobile contexts, such as automobiles or other vehicles (e.g., land, water, air, space) and portable devices e.g., smartphones, tablets, and MP3 players).

Targeted advertising, marketing, and sales could be an integral part of the system. Lighting/sound/smell/temperature/climate can be activated in retail stores depending on the state of mind or being of potential customers. For example, if the device indicates stress, the stress-relief products sections of stores could light up or other directional cues may be engaged in suitably equipped stores, if an environmental interaction unit detects a feeling of hunger or thirst, a food or beverage section of a store could light up or other directional cues may be engaged. This could also be implemented in the online context, when people are shopping or browsing the Internet or digital marketplaces via their computer, mobile device, or other console type. In all contexts (brick-and-mortar or online/digital), retailers, sellers, manufactures, or others could suggest specific products or services in response to readings conveyed by the environmental interaction unit. Commercials or advertisements on TV, radio, or online may be targeted to individuals with specific states of mind or being.

The system may be useful not only for responding to the state of being associated with a particular individual. In some embodiments, the system may respond to the determined state of being for multiple individuals. For example, the being states of a plurality of users may be collected and use to control one or more responses of at least one environmental control device. The response may be determined based on a single individual from among the group (e.g., determined or selected at random or determined or selected based on a predetermined hierarchy among the individuals in the group). Alternatively, the response may be based on an averaged or collective state of being of the group determined by aggregating the individual states of being or environmental control signals transmitted by the individual environmental interaction units 10. For example, at a concert venue, an array of lights or an array of speakers may be controlled by adjusting light color, speaker volume, light direction, etc. in response to the collective determined states of being for the individuals attending the concert (or in some cases watching a concert or event online, where environmental interaction units 10 have Wi-Fi/Internet connections, for example). Crowd-generated environmental responses may be achieved by collecting data from a plurality of environmental interaction devices and generating statistical charts based on the collected data (mean, median, standard deviation). These results may then be used to provide feedback to the system owner (overall excitement in the crowd, crowd boredom, etc.), and suitable changes in lighting, sound, content, entertainment, etc. may be applied to the environment of the crowd.

The monitoring of groups of individuals may be accomplished on any desirable size or scale, and the system responses may be based on the number of tracked individuals in a particular environment. At a home, where the number of people in a room is likely limited (as compared to a concert hall), the state of mind or being of different people could be assigned different weights, such that "Person A" has the most weight in deciding the environment in his/her own bedroom, while 'Person B' would have more weight on the environment in "Room B." Parents may have more influence than kids when determining the state of the environment in a common area (i.e., family room, living room, kitchen, dining room). These weights can be programmed with the use of a portable or other device, such as a phone or smartphone, tablet, computer, remote control, DVR or cable TV console, video game console, electronic appliance interface, etc. A similar approach can be implemented in office, retail, and other commercial spaces, where individual users would have a larger weighting power in their own offices, spaces, or cubicles and "visitors" would have a lower level of influence.

The combination of multiple readings in a neutral environment, where no one user has more weight than others in deciding the effects on the surrounding environment, can be used to assess group dynamics. Examples include concert halls, political rallies, celebrations, sport arenas and complexes, conferences/meetings, among any other public, or private gatherings in buildings, churches, structures of any type, or open public or private space, such as parks and gardens. For instance, the information can then be used to determine in real time whether the message or content communicated during such gatherings (e.g., political rallies, concerts) is coming across in a positive, negative, or other way so the delivery of the message or content can be adjusted in real-time, or other set intervals, or whether the crowds are excited or otherwise influenced by the events they are watching or participating in (sports, concerts) such that light, volume, temperature, climate, entertainment, content, or other stimuli in the structure, open space, or area can be adjusted, modified, or continued accordingly.

The system can be configured to assign priorities such that some users have more influence than others, and to prevent unauthorized access to a network of devices. For example, devices worn by parents can have more weight than those worn by teenagers when deciding how the environment is affected. Devices worn by the boss in an office may override those worn by employees.

Users can be assigned priorities/weights for pairings of environmental interaction units with different environments. For example, as noted above, one user may have the highest weight in his/her own room, while the same user may have a lower priority in the parents' or siblings' room. Priorities for each environmental interaction unit and environment pairing can be set from commands issued from a portable device such as a smart phone, tablet, or a dedicated device. Password control may ensure than only authorized people can set weights and priorities. The system can be configured with encryption to prevent unauthorized access to a network. The weights may be selected by the owner of a network. He or she can assign any one user (or users) to have a certain weight relative to particular places. People not registered as users (e.g., guests) can be assigned a lower weight or no weight at all relative to various environments.

Other examples of environmental control devices may include internal and/or external lighting associated with buildings, skyscrapers, structures, or open spaces, which could change in response to device readings of a user or group of users within a given proximity to the building, structure, or space. For example, landmark/building colors may change depending on a collective state of mind or being of users within a defined proximate distance (or as received via smartphones, tablets, computers from points around the globe—all based on readings from individual environmental interaction units).

Further examples of environments for which at least one control may be implemented based on determined being state of an individual or group may include elevators, doctor's offices, waiting rooms, indoor/outdoor party venues, kids playgrounds, schools/classrooms, locker rooms, airplanes, restaurants/bars (individually controlling the light wavelength/intensity for each table), places of worship, clubs, funeral homes, farms, theaters, public transportation (cars/trains/buses/watercraft/aircraft), other private and public places, etc. Locations where sensitive information or personnel are located (Armed Forces bases, government facilities, high security areas, nuclear plants, data centers, mission-critical areas, air-traffic control, prisons, jails etc.) can also benefit by the monitoring of the state of mind or state of being of people attempting to enter the facilities. For instance, a detection of distress or anger on an individual could increase the alert level of the security personnel such that additional security steps implemented relative to the individual.

A system may detect that a person has woken up in the middle of the night (e.g., when heart rate is low and movement is low for an extended period followed by a sudden increase, or when a repetitive sound, such as snoring, suddenly stops). The system may response by turning on a night lamp and setting the color of the light such that red wavelengths are minimized, while the blue wavelengths are enhanced. Such a setting may facilitate going back to sleep if desired. The response of the system when the person wakes up in the morning, however, may be to turn on a night lamp and adjust the color such that the hue will tend towards the red spectrum to help the person wake up. A system that has detected that a person is stressed may configure the lights in a room to a soft/warm color. It could also change the volume of a TV/radio receiver or music player, and could select soothing music as predefined by the user.

The use of the technology can be further expanded to incorporate monitoring of livestock and animals. It has been documented in the available literature that stress conditions affect animal growth and health. Monitoring the state of being of an animal, or group of animals, could allow for modification or continuation of, for example, light, feed, water, temperature, climate, and sounds.

Figure 4:
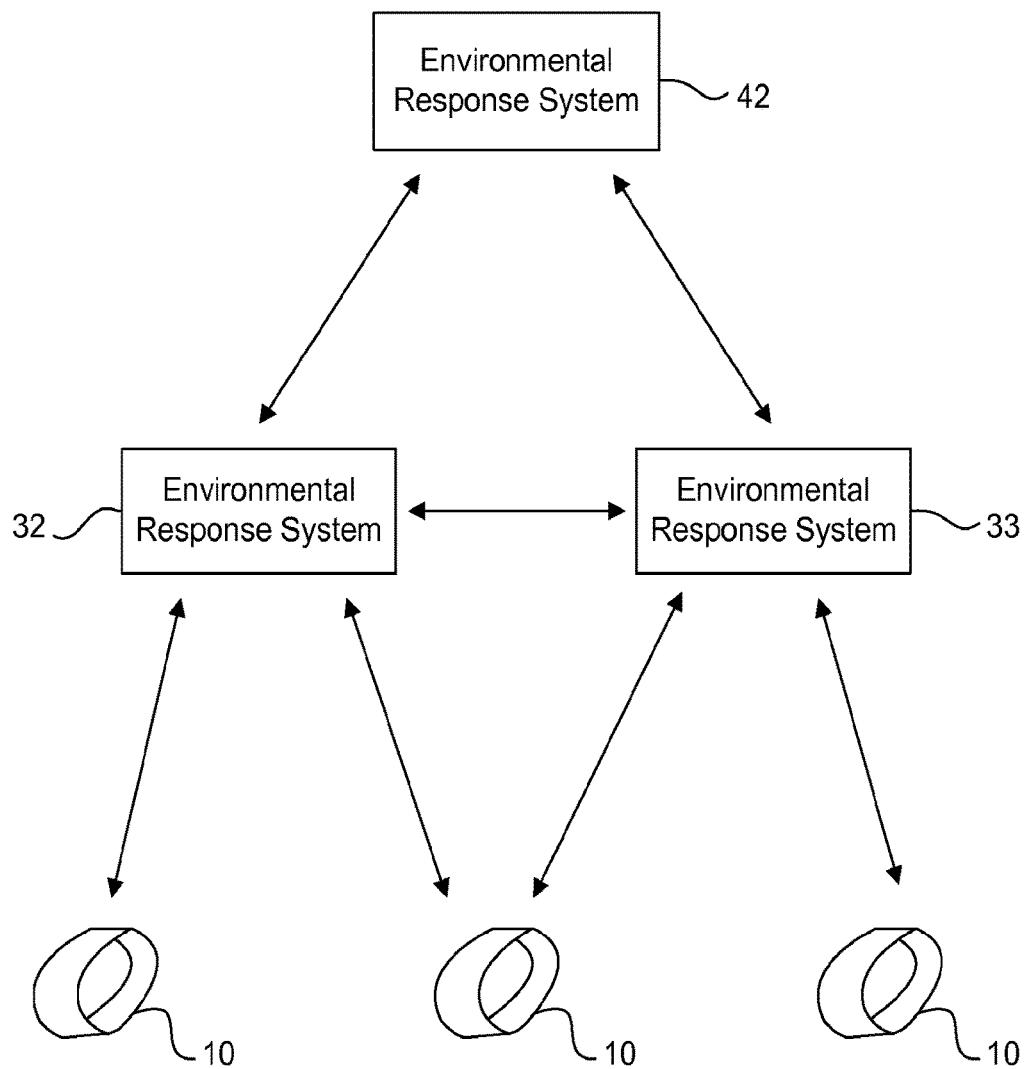
FIG. 4 is a representation of an environmental response architecture according to an exemplary disclosed embodiment.

FIG. 4 provides a diagrammatic representation of an environmental response architecture according to an exemplary disclosed embodiment. In this embodiment, environmental response system 42 operates a slave to either environmental response system 32 or environmental response system 33. In other words, rather than receiving a control signal or a detected being state from an environmental interaction unit 10, this information may be provided to response system 42 via either of response systems 32 or 33. In some embodiments, environmental response systems 32 and 33 may also share control signals or being states collected from individual environmental interaction units. By sharing information in this way, aggregated responses may be achieved based on the being states of multiple users and/or uniformity in responses may be achieved across multiple environmental response systems. In such embodiments, the network of devices to be controlled can be assembled into an active network by detecting "neighbor devices."

Figure 5:
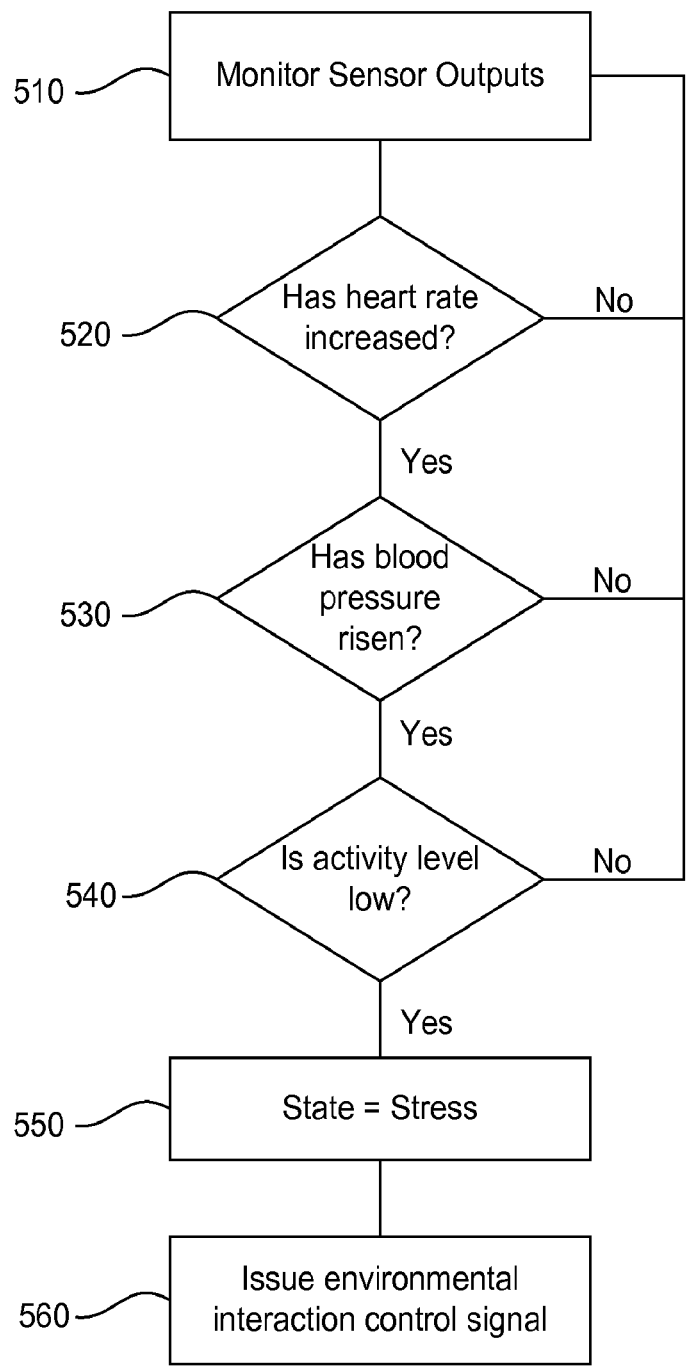
FIG. 5 is a flow chart illustrating an exemplary operation of an environmental response architecture according to an exemplary disclosed embodiment.

FIG. 5 is a flow chart illustrating an exemplary operation of an environmental response architecture according to an exemplary disclosed embodiment. At step 510, the sensor outputs from the plurality of sensors 20 may be monitored. At step 520 a determination is made regarding whether a user of an environmental interaction unit has experienced an increase in heart rate (e.g., by a threshold amount). If no, then the process returns to step 510. If yes, then at step 530, a determination is made regarding whether the user's blood pressure has risen (e.g., by a threshold amount). If no, then the process returns to step 510. If yes, then a determination is made at step 540 regarding whether the user is in a state of low activity (e.g., not exercising). If no, then the process returns to step 510. If yes, then a determination may be made at step 550 that the user's state of being is defined as stressed. At step 560, an environmental interaction control signal may be issued, which may include the determined state of being, for example, in order to cause a response by an environmental response unit including at least one change in an environmental condition.

It will be apparent to those skilled in the art that various modifications and variations can be made in the disclosed sensor unit without departing from the scope of the disclosure. Other embodiments of the disclosed systems and methods will be apparent to those skilled in the art from consideration of the specification and practice of the disclosure disclosed herein.

What is claimed is:

1. A wearable environmental interaction unit, comprising:
a plurality of sensors each being configured to provide an output indicative of at least one physiological aspect of an individual, wherein the plurality of sensors include at least a heart rate sensor and a motion sensor;
a transmitter to establish a wireless communication path between the wearable environmental interaction unit and at least one environmental response unit located remotely with respect to the wearable environmental interaction unit; and
a microcontroller programmed to:
receive a first plurality of output values from the heart rate sensor during a first time period when the individual is at rest and determine a baseline heart rate level for the individual based on the first plurality of output values from the heart rate sensor;
receive, during a second time period different than the first time period, a second plurality of output values from the heart rate sensor and a third plurality of output values from the motion sensor;
determine whether the individual is experiencing a stressed state of being based on the third plurality of output values associated with the motion sensor and based on a comparison of the baseline heart rate level for the individual to an indicator of current heart rate associated with the second plurality of output values from the heart rate sensor;
generate an environmental interaction control signal associated with the determined stressed state of the individual; and
cause the transmitter to transmit the environmental interaction control signal to the at least one environmental response unit via the wireless communication path, the environmental interaction control signal being configured to cause a response by the environmental response unit including at least one change in a condition of an environment of the individual.

2. The wearable environmental interaction unit of claim 1, wherein the change in the condition of the environment of the individual includes one or more of a change in lighting or a change in sound within the environment of the individual.

3. The wearable environmental interaction unit of claim 1, wherein the change in the condition of the environment of the individual includes a change in lighting color or lighting intensity within the environment of the individual.

4. The wearable environmental interaction unit of claim 1, wherein the change in the condition of the environment of the individual includes a change in a sound volume or music type within the environment of the individual.

5. The wearable environmental interaction unit of claim 1, wherein the change in the condition of the environment of the individual includes at least one of a change in temperature, change in humidity, an adjustment of vehicle speed or control, a locking of a door, locking of a window, activation of a barrier, a presentation of a targeted advertisement, a presentation of an audible alert, a presentation of a visible alert, activation of product displays, a presentation of selected content via radio, a presentation of selected content via television, a presentation of selected content via the Internet, a presentation of content recommendations, or a change in smell or fragrance within the environment of the individual.

6. The wearable environmental interaction unit of claim 1, wherein the wireless communication path includes at least one of a radio frequency or optical connection.

7. The wearable environmental interaction unit of claim 1, wherein motion sensor includes an accelerometer, the heart rate sensor includes at least one of an infrared transceiver, an EKG monitor, or and EEG monitor, and the plurality of sensors further includes at least one of a temperature sensor, a $CO_2$ sensor, a microphone, a photodetector, a GPS sensor, or a chemical sensor.

8. The wearable environmental interaction unit of claim 1, wherein the determination of whether the individual is experiencing a stressed state includes a determination that a current heart rate of the individual, determined based on the second plurality of output values from the heart rate sensor, is elevated relative to the determined baseline heart rate for the individual, but that an activity level for the individual, determined based on the second plurality of output values associated with the motion sensor, does not indicate an increase in activity level for the individual.

9. The wearable environmental interaction unit of claim 1, wherein the plurality of sensors further includes a skin conductivity sensor, and wherein the microcontroller is further programmed to:
receive a fourth plurality of output values from the skin conductivity sensor during the time period when the individual is at rest and determine a baseline skin conductivity level for the individual based on the fourth plurality of output values from the skin conductivity sensor;
receive during the second time period, a fifth plurality of output values from the skin conductivity sensor; and
determine whether the individual is experiencing a stressed state of being based on the third plurality of output values associated with the motion sensor, a comparison of the baseline heart rate level for the individual to an indicator of current heart rate associated with the second plurality of output values from the heart rate sensor, and a comparison of the baseline skin conductivity level for the individual to an indicator of current skin conductivity level associated with the fifth plurality of output values from the skin conductivity sensor.

10. The wearable environmental interaction unit of claim 9, wherein the determination of whether the individual is experiencing a stressed state is associated with whether the comparison of the baseline heart rate to the indicator of current heart rate shows a greater than 30% increase in heart rate over the baseline heart rate level for the individual, whether the comparison of the baseline skin conductivity to the indicator of current skin conductivity level shows a greater than 25% increase in skin conductivity over the baseline skin conductivity level for the individual, and an activity level for the individual, determined based on the third plurality of output values associated with the motion sensor, does not indicate an increase in activity level for the individual.

11. An environmental response system comprising:
one or more environmental control devices configured to change at least one aspect of an environment;
a transceiver to receive at least one of an environmental control signal or a state of being indicator from two or more environmental interaction units each of the two or more environmental interaction units being associated with a different individual; and
a processing device programmed to:
receive at least one of the environmental control signals or the state of being indicators from the two or more environmental interaction units;
determine a collective state of being associated with the two or more environmental interaction units by aggregating the environmental control signals or the individual state of being indicators received from the two or more environmental interaction units;
determine an environmental change to make based on the determined collective state of being associated with the two or more environmental interaction units; and
cause the environmental change through control of the one or more environmental control devices.

12. The environmental response system of claim 11, wherein the environmental change includes at least one of a change in sound or a change in lighting associated with the environment.

13. The environmental response system of claim 11, wherein the one or more environmental control devices include at least one of a light or a sound speaker.

14. The environmental response system of claim 11, wherein the one or more environmental control devices include at least one of a throttle, brakes, steering mechanism, locks, air-bag, or comfort control for a vehicle, a display screen, a door or window lock control, a barrier activation, a thermostat, humidifier, a radio, a television, a tablet, a smart phone, or a smell or fragrance emitter.

15. The environmental response system of claim 11, wherein the environmental control signal specifies a state of being for an individual, the state of being including at least one of a normal, stressed, calm, happy, angry, alert, sleepy, inattentive, or excited state.

\* \* \* \* \*